(12) United States Patent
Ruchala et al.

(10) Patent No.: US 8,767,917 B2
(45) Date of Patent: *Jul. 1, 2014

(54) SYSTEM AND METHOD OF DELIVERING RADIATION THERAPY TO A MOVING REGION OF INTEREST

(75) Inventors: Kenneth J. Ruchala, Madison, WI (US); Gustavo H. Olivera, Madison, WI (US); Weiguo Lu, Madison, WI (US); Eric Schnarr, McFarland, WI (US); John H. Hughes, Madison, WI (US); Jeffrey M. Kapatoes, Madison, WI (US); Thomas R. Mackie, Verona, WI (US); Paul J. Reckwerdt, Madison, WI (US)

(73) Assignee: Tomotherapy Incorpoated, Madison, WI (US)

(*) Notice: Subject to any disclaimer, the term of this patent is extended or adjusted under 35 U.S.C. 154(b) by 884 days.

This patent is subject to a terminal disclaimer.

(21) Appl. No.: 11/459,074

(22) Filed: Jul. 21, 2006

(65) Prior Publication Data
US 2007/0076846 A1    Apr. 5, 2007

Related U.S. Application Data

(60) Provisional application No. 60/701,541, filed on Jul. 22, 2005, provisional application No. 60/701,580, filed on Jul. 22, 2005.

(51) Int. Cl.
*A61N 5/10*    (2006.01)

(52) U.S. Cl.
USPC .......................................................... 378/65

(58) Field of Classification Search
USPC .................... 600/315, 407, 427; 378/65, 901
See application file for complete search history.

(56) References Cited

U.S. PATENT DOCUMENTS

| | | | |
|---|---|---|---|
| 3,949,265 A | 4/1976 | Holl | |
| 3,964,467 A | 6/1976 | Rose | |
| 4,006,422 A | 2/1977 | Schriber | |
| 4,032,810 A | 6/1977 | Eastham et al. | |
| 4,149,081 A | 4/1979 | Seppi | |
| 4,181,894 A | 1/1980 | Pottier | |

(Continued)

FOREIGN PATENT DOCUMENTS

| | | |
|---|---|---|
| CA | 2091275 | 9/1993 |
| CA | 2180227 | 12/1996 |

(Continued)

OTHER PUBLICATIONS

Ronald D. Rogus et al., "Accuracy of a Photogrammetry-Based Patient Positioning and Monitoring System for Radiation Therapy," Medical Physics, vol. 26, Issue 5, May 1999.

(Continued)

*Primary Examiner* — Elmer Chao
(74) *Attorney, Agent, or Firm* — Michael Best & Friedrich LLP

(57) ABSTRACT

A system for and method of delivering radiation therapy to a moving region of interest is disclosed. The method, in one implementation, includes the acts of generating a plurality of treatment plans for providing radiation therapy, delivering radiation therapy to the patient following one of the plurality of treatment plans, monitoring the patient while providing radiation therapy, and changing the treatment plan based at least in part on monitoring the patient.

16 Claims, 12 Drawing Sheets

(56) References Cited

U.S. PATENT DOCUMENTS

| | | |
|---|---|---|
| 4,189,470 A | 2/1980 | Rose |
| 4,208,185 A | 6/1980 | Sawai et al. |
| 4,273,867 A | 6/1981 | Lin et al. |
| 4,314,180 A | 2/1982 | Salisbury |
| 4,335,465 A | 6/1982 | Christiansen et al. |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,455,609 A | 6/1984 | Inamura et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,044,354 A | 9/1991 | Goldhorn et al. |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,117,829 A | 6/1992 | Miller et al. |
| 5,124,658 A | 6/1992 | Adler |
| 5,138,647 A | 8/1992 | Nguyen et al. |
| 5,210,414 A | 5/1993 | Wallace et al. |
| 5,250,388 A | 10/1993 | Schoch, Jr. et al. |
| 5,317,616 A | 5/1994 | Swerdloff et al. |
| 5,332,908 A | 7/1994 | Weidlich |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,446,548 A | 8/1995 | Gerig et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,511,549 A | 4/1996 | Legg et al. |
| 5,523,578 A | 6/1996 | Herskovic |
| 5,528,650 A | 6/1996 | Swerdloff et al. |
| 5,548,627 A | 8/1996 | Swerdloff et al. |
| 5,552,605 A | 9/1996 | Arata |
| 5,576,602 A | 11/1996 | Hiramoto et al. |
| 5,578,909 A | 11/1996 | Billen |
| 5,579,358 A | 11/1996 | Lin |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,823,192 A | 10/1998 | Kalend et al. |
| 5,834,454 A | 11/1998 | Kitano et al. |
| 5,835,562 A | 11/1998 | Ramsdell et al. |
| 5,836,905 A | 11/1998 | Lemelson et al. |
| 5,842,175 A | 11/1998 | Andros et al. |
| 5,866,912 A | 2/1999 | Slater et al. |
| 5,870,447 A | 2/1999 | Powell et al. |
| 5,870,697 A | 2/1999 | Chandler et al. |
| 5,877,023 A | 3/1999 | Sautter et al. |
| 5,877,192 A | 3/1999 | Lindberg et al. |
| 5,912,134 A | 6/1999 | Shartle |
| 5,920,601 A | 7/1999 | Nigg et al. |
| 5,949,080 A | 9/1999 | Ueda et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,144,875 A | 11/2000 | Schweikard et al. |
| 6,152,599 A | 11/2000 | Salter |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,316,776 B1 | 11/2001 | Hiramoto et al. |
| 6,319,469 B1 | 11/2001 | Mian et al. |
| 6,322,249 B1 | 11/2001 | Wofford et al. |
| 6,331,194 B1 | 12/2001 | Elizondo-Decanini et al. |

(56) References Cited

U.S. PATENT DOCUMENTS

| | | |
|---|---|---|
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,407,505 B1 | 6/2002 | Bertsche |
| 6,417,178 B1 | 7/2002 | Klunk et al. |
| 6,424,856 B1 | 7/2002 | Vilsmeier et al. |
| 6,428,547 B1 | 8/2002 | Vilsmeier et al. |
| 6,433,349 B2 | 8/2002 | Akiyama et al. |
| 6,438,202 B1 | 8/2002 | Olivera et al. |
| 6,455,844 B1 | 9/2002 | Meyer |
| 6,462,490 B1 | 10/2002 | Matsuda et al. |
| 6,465,957 B1 | 10/2002 | Whitham et al. |
| 6,466,644 B1 | 10/2002 | Hughes et al. |
| 6,469,058 B1 | 10/2002 | Grove et al. |
| 6,472,834 B2 | 10/2002 | Hiramoto et al. |
| 6,473,490 B1 | 10/2002 | Siochi |
| 6,475,994 B2 | 11/2002 | Tomalia et al. |
| 6,482,604 B2 | 11/2002 | Kwon |
| 6,484,049 B1 | 11/2002 | Seeley et al. |
| 6,484,144 B2 | 11/2002 | Martin et al. |
| 6,487,274 B2 | 11/2002 | Bertsche |
| 6,493,424 B2 | 12/2002 | Whitham |
| 6,497,358 B1 | 12/2002 | Walsh |
| 6,498,011 B2 | 12/2002 | Hohn et al. |
| 6,500,343 B2 | 12/2002 | Siddiqi |
| 6,504,899 B2 | 1/2003 | Pugachev et al. |
| 6,510,199 B1 | 1/2003 | Hughes et al. |
| 6,512,942 B1 | 1/2003 | Burdette et al. |
| 6,516,046 B1 | 2/2003 | Frohlich et al. |
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,539,247 B2 | 3/2003 | Spetz |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,723,334 B1 | 4/2004 | McGee et al. |
| 6,757,355 B1 | 6/2004 | Siochi |
| 6,760,402 B2 | 7/2004 | Ghelmansarai |
| 6,774,383 B2 | 8/2004 | Norimine et al. |
| 6,787,771 B2 | 9/2004 | Bashkirov et al. |
| 6,787,983 B2 | 9/2004 | Yamanobe et al. |
| 6,788,764 B2 | 9/2004 | Saladin et al. |
| 6,792,073 B2 | 9/2004 | Deasy et al. |
| 6,796,164 B2 | 9/2004 | McLoughlin et al. |
| 6,800,866 B2 | 10/2004 | Amemiya et al. |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 * | 1/2005 | Jaffray et al. ............ 378/65 |
| 6,844,689 B1 | 1/2005 | Brown et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 | 5/2005 | Pankratov et al. |
| 6,922,455 B2 | 7/2005 | Jurczyk et al. |
| 6,929,398 B1 | 8/2005 | Tybinkowski et al. |
| 6,936,832 B2 | 8/2005 | Norimine et al. |
| 6,955,464 B1 | 10/2005 | Tybinkowski et al. |
| 6,961,405 B2 | 11/2005 | Scherch |
| 6,963,171 B2 | 11/2005 | Sagawa et al. |
| 6,974,254 B2 | 12/2005 | Paliwal et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,112,924 B2 | 9/2006 | Hanna |
| 7,130,372 B2 | 10/2006 | Kusch et al. |
| 7,154,991 B2 | 12/2006 | Earnst et al. |
| 7,177,386 B2 | 2/2007 | Mostafavi et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 | 4/2007 | Baier et al. |
| 7,221,733 B1 | 5/2007 | Takai et al. |
| 7,252,307 B2 | 8/2007 | Kanbe et al. |
| 7,257,196 B2 | 8/2007 | Brown et al. |
| 7,295,648 B2 | 11/2007 | Brown |
| 7,450,687 B2 | 11/2008 | Yeo et al. |
| 7,469,035 B2 | 12/2008 | Keall et al. |
| 7,492,858 B2 | 2/2009 | Partain et al. |
| 7,519,150 B2 | 4/2009 | Romesberg et al. |
| 7,551,717 B2 | 6/2009 | Tome et al. |
| 7,613,501 B2 | 11/2009 | Scherch |
| 7,708,682 B2 | 5/2010 | Pekar et al. |
| 7,831,289 B2 | 11/2010 | Riker et al. |
| 7,881,431 B2 | 2/2011 | Aoi et al. |
| 7,983,380 B2 | 7/2011 | Guertin et al. |
| 8,073,104 B2 | 12/2011 | Yan et al. |
| 8,085,899 B2 | 12/2011 | Nord et al. |
| 2002/0007918 A1 | 1/2002 | Owen et al. |
| 2002/0077545 A1 | 6/2002 | Takahashi et al. |
| 2002/0080915 A1 | 6/2002 | Frohlich |
| 2002/0085668 A1 | 7/2002 | Blumhofer et al. |
| 2002/0091314 A1 | 7/2002 | Schlossbauer et al. |
| 2002/0115923 A1 | 8/2002 | Erbel |
| 2002/0120986 A1 | 9/2002 | Erbel et al. |
| 2002/0122530 A1 | 9/2002 | Erbel et al. |
| 2002/0136439 A1 | 9/2002 | Ruchala et al. |
| 2002/0150207 A1 | 10/2002 | Kapatoes et al. |
| 2002/0187502 A1 | 12/2002 | Waterman et al. |
| 2002/0193685 A1 * | 12/2002 | Mate et al. ............ 600/424 |
| 2003/0007601 A1 | 1/2003 | Jaffray et al. |
| 2003/0031298 A1 | 2/2003 | Xing |
| 2003/0048868 A1 | 3/2003 | Bailey et al. |
| 2003/0086527 A1 | 5/2003 | Speiser et al. |
| 2003/0105650 A1 | 6/2003 | Lombardo et al. |
| 2003/0174872 A1 | 9/2003 | Chalana et al. |
| 2004/0010418 A1 | 1/2004 | Buonocore et al. |
| 2004/0024300 A1 | 2/2004 | Graf |
| 2004/0068182 A1 | 4/2004 | Misra |
| 2004/0071337 A1 | 4/2004 | Jeung et al. |
| 2004/0096033 A1 * | 5/2004 | Seppi et al. ............ 378/65 |
| 2004/0116804 A1 | 6/2004 | Mostafavi |
| 2004/0165696 A1 | 8/2004 | Lee |
| 2004/0202280 A1 | 10/2004 | Besson |
| 2004/0230115 A1 | 11/2004 | Scarantino et al. |

(56) References Cited

U.S. PATENT DOCUMENTS

| | | | |
|---|---|---|---|
| 2004/0254448 A1 | 12/2004 | Amies et al. | |
| 2004/0254492 A1 | 12/2004 | Zhang et al. | |
| 2004/0254773 A1 | 12/2004 | Zhang et al. | |
| 2004/0264640 A1 | 12/2004 | Myles | |
| 2005/0013406 A1 | 1/2005 | Dyk et al. | |
| 2005/0031181 A1 | 2/2005 | Bi et al. | |
| 2005/0080332 A1 | 4/2005 | Shiu et al. | |
| 2005/0096515 A1 | 5/2005 | Geng | |
| 2005/0123092 A1 | 6/2005 | Mistretta et al. | |
| 2005/0143965 A1 | 6/2005 | Failla et al. | |
| 2005/0180544 A1 | 8/2005 | Sauer et al. | |
| 2005/0197564 A1 | 9/2005 | Dempsey | |
| 2005/0201515 A1 | 9/2005 | Mitschke | |
| 2005/0201516 A1 | 9/2005 | Ruchala et al. | |
| 2005/0251029 A1* | 11/2005 | Khamene et al. | 600/427 |
| 2006/0074292 A1 | 4/2006 | Thomson et al. | |
| 2006/0083349 A1 | 4/2006 | Harari et al. | |
| 2006/0100738 A1 | 5/2006 | Alsafadi et al. | |
| 2006/0133568 A1 | 6/2006 | Moore | |
| 2006/0193429 A1 | 8/2006 | Chen | |
| 2006/0193441 A1 | 8/2006 | Cadman | |
| 2006/0241332 A1 | 10/2006 | Klein et al. | |
| 2006/0285639 A1 | 12/2006 | Olivera et al. | |
| 2006/0285640 A1 | 12/2006 | Nizin et al. | |
| 2006/0293583 A1* | 12/2006 | Saracen et al. | 600/407 |
| 2007/0041494 A1 | 2/2007 | Ruchala et al. | |
| 2007/0041495 A1 | 2/2007 | Olivera et al. | |
| 2007/0041496 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0088573 A1 | 4/2007 | Ruchala et al. | |
| 2007/0104316 A1 | 5/2007 | Ruchala et al. | |
| 2007/0127623 A1 | 6/2007 | Goldman et al. | |
| 2007/0127790 A1 | 6/2007 | Lau et al. | |
| 2007/0165920 A1 | 7/2007 | Gering et al. | |
| 2007/0189591 A1 | 8/2007 | Lu et al. | |
| 2007/0195922 A1 | 8/2007 | Mackie et al. | |
| 2007/0195929 A1 | 8/2007 | Ruchala et al. | |
| 2007/0195930 A1 | 8/2007 | Kapatoes et al. | |
| 2007/0197908 A1 | 8/2007 | Ruchala et al. | |
| 2007/0201613 A1 | 8/2007 | Lu et al. | |
| 2007/0211857 A1 | 9/2007 | Urano et al. | |
| 2007/0242796 A1* | 10/2007 | Vengrinovich et al. | 378/11 |
| 2008/0002809 A1 | 1/2008 | Bodduluri | |
| 2008/0002811 A1 | 1/2008 | Allison | |
| 2008/0008291 A1 | 1/2008 | Alakuijala et al. | |
| 2008/0031406 A1 | 2/2008 | Yan et al. | |
| 2008/0049896 A1 | 2/2008 | Kuduvalli | |
| 2008/0064953 A1 | 3/2008 | Falco | |
| 2008/0279328 A1 | 11/2008 | Zeitler et al. | |
| 2009/0041200 A1 | 2/2009 | Lu et al. | |
| 2009/0116616 A1 | 5/2009 | Lu et al. | |
| 2009/0187422 A1 | 7/2009 | Kaus et al. | |
| 2009/0252291 A1 | 10/2009 | Lu et al. | |
| 2010/0053208 A1 | 3/2010 | Menningen et al. | |
| 2010/0054413 A1 | 3/2010 | Sobering et al. | |
| 2011/0019889 A1 | 1/2011 | Gering et al. | |
| 2011/0112351 A1 | 5/2011 | Fordyce et al. | |

FOREIGN PATENT DOCUMENTS

| | | |
|---|---|---|
| EP | 1419801 | 3/2010 |
| JP | 63209667 | 8/1988 |
| JP | 6007464 | 1/1994 |
| JP | 10052421 | 2/1998 |
| JP | 10501151 | 2/1998 |
| JP | 11244401 | 9/1999 |
| JP | 2001161839 | 6/2001 |
| JP | 2001340474 | 12/2001 |
| JP | 2002186678 | 7/2002 |
| JP | 2002210029 | 7/2002 |
| JP | 2002522128 | 7/2002 |
| JP | 2002522129 | 7/2002 |
| JP | 2002355321 | 12/2002 |
| JP | 2003523220 | 8/2003 |
| JP | 2004166975 | 6/2004 |
| JP | 2004275636 | 10/2004 |
| JP | 2004321502 | 11/2004 |
| JP | 2005160804 | 6/2005 |
| JP | 2005518908 | 6/2005 |
| JP | 2007509644 | 4/2007 |
| JP | 2007516743 | 6/2007 |
| JP | 2007526036 | 9/2007 |
| TW | 300853 | 3/1997 |
| WO | 9202277 | 2/1992 |
| WO | 0007669 | 2/2000 |
| WO | 0054689 | 9/2000 |
| WO | 03076003 | 9/2003 |
| WO | 03092789 | 11/2003 |
| WO | 2004057515 | 7/2004 |
| WO | 2004066211 | 8/2004 |
| WO | 2004080522 | 9/2004 |
| WO | 2004105574 | 12/2004 |
| WO | 2005057463 | 6/2005 |
| WO | 2007014026 | 2/2007 |
| WO | 2007014094 | 2/2007 |
| WO | 2007079854 | 7/2007 |
| WO | 2007133932 | 11/2007 |

OTHER PUBLICATIONS

D. Rueckert et al., "Nonrigid Registration Using Free-Form Deformations: Application to Breast MR Images," IEEE Transactions on Medical Imaging, vol. 18, No. 8, Aug. 1999.

Yuan-Nan Young, "Registraion-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001. (Note: the title of the periodical and the date listed are from the International Search Report, however they do not appear on the article itself.).

PCT/US06/28554 International Search Report and Written Opinion mailed Oct. 2, 2007.

Ruchala, Kenneth, et al., "Adaptive IMRT with Tomotherapy", RT Image, vol. 14, No. 25, pp. 14-18, Jun. 18, 2001.

Marcelo Bertalmio, et al., "Morphing Active Contours", IEEE Transactions on Pattern Analysis and Machine Intelligence, vol. 22, No. 7, pp. 733-737, Jul. 2000.

Lu, W., et al., "Automatic Re-Contouring in 4D Radiotherapy", Physical Medical Biology, Mar. 7, 2006, 51(5): 1077-99.

Lu, W., et al., 2004 Automatic Re-Contouring for 4-D Planning and Adaptive Radiotherapy, The 90th RSNA Meeting, Chicago, Illinois, (abstract: Radiology 227 p. 543).

Lu, W., et al., 2004 Automatic Re-Contouring Regions of Interest Based on Deformable Registration and Surface Reconstruction, AAPM 2004, (abstract: Medical Physics 31, 1845-6).

Purdy, James, "3D Treatment Planning and Intensity-Modulated Radiation Therapy," Oncology, vol. 13, No. 10, suppl. 5 (Oct. 1999).

Bert, Christoph, et al., "4D Treatment Planning for Scanned Ion Beams", BioMed Central, Radiation Oncology, 2:24, available online at: <http://www.ro-journal.com/content/2/1/24>, 2007.

Yu, Cedric X., et al., "A Method for Implementing Dynamic Photon Beam Intensity Modulation using Independent Jaws and a Multileaf Collimator," Phys. Med. Biol. 40. 1995: 769-787.

Keall, Paul, "4-Dimensional Computed Tomography Imaging and Treatment Planning," Seminars in Radiation Oncology, vol. 14, No. 1, Jan. 2004; pp. 81-90.

Mackie, T. Rockwell et al., "Tomotherapy" Seminars in Radiation Oncology, vol. 9, No. 1, Jan. 1, 1999, pp. 108-117, XP002603992.

Miller, Karen, "The Phantom Torso", RT Image, vol. 14 No. 25, Jun. 18, 2001.

Song, Yulin, et al., "From Intensity Modulated Radiation Therapy to 4D Radiation Therapy—An Advance in Targeting Mobile Lung

(56) References Cited

OTHER PUBLICATIONS

Tumors", Proceedings of the 29th Annual International Conference of the IEEE EMBS Cite Internationale, Lyon, France, Aug. 23-26, pp. 226-229, 2007.
Extended European Search Report for European Application No. 06800244.3 dated Sep. 23, 2009 (6 pages).
European Examination Report for European Application No. 06800244.3 dated Aug. 6, 2010 (5 pages).
Extended European Search Report for European Application No. 08006234.2 dated Sep. 23, 2009 (7 pages).
Office Action from Australian Patent Office for Application No. 2006272742 dated Sep. 15, 2010 (3 pages).
Office Action from Chinese Patent Office for Application No. 200680034564.0 dated Jun. 11, 2010 (6 pages).
Office Action from Chinese Patent Office for Application No. 200680034564.0 dated Dec. 5, 2011 (10 pages).
Office Action from European Patent Office for Application No. 06800244.3 dated Feb. 24, 2011 (4 pages).
Office Action from Japanese Patent Office for Application No. 2008-523024 dated Dec. 2, 2011 (2 pages).
Mackie, T. Rockwell et al., "Tomotherapy: Rethinking the Processes of Radiotherapy," XIIth ICCR, May 27-30, 1997.
Fang, Guang Y. et al., "Software system for the UW/GE tomotherapy prototype," XIIth ICCR, May 27-30, 1997.
Rietzel, Eike et al., "Four-Dimensional Image-Based Treatment Planning: Target Volume Segmentation and Dose Calculation in the Presence of Respiratory Motion," International Journal of Radiation: Oncology Biology Physics, vol. 61, No. 5, pp. 1535-1550 (Apr. 1, 2005).
Office action from European Patent Office for European Application No. 06800244.3 dated Mar. 26, 2012.
Office Action from Chinese Patent Office for Application No. 200680034564.0 dated Jun. 28 2012.
Office Action from Japanese Patent Office for Application No. 2008-523024 dated Nov. 16, 2012.
Extended European Search Report for European Application No. 12179427.5 dated Jan. 21, 2013.

* cited by examiner

SYSTEM AND METHOD OF DELIVERING RADIATION THERAPY TO A MOVING REGION OF INTEREST

RELATED APPLICATIONS

This application claims the benefit of U.S. Provisional Patent Application No. 60/701,541; titled SYSTEM AND METHOD OF DELIVERING RADIATION THERAPY TO A MOVING TARGET; filed on Jul. 22, 2005; and the benefit of U.S. Provisional Patent Application No. 60/701,580; filed Jul. 22, 2005; titled SYSTEM AND METHOD FOR FEEDBACK GUIDED QUALITY ASSURANCE AND ADAPTATIONS TO RADIATION THERAPY TREATMENT; all of which are incorporated herein by reference.

BACKGROUND

Recently, radiation therapy practice has incorporated improvements in computers and networking, radiation therapy treatment planning software, and medical imaging modalities (such as, computed tomography ("CT"), magnetic resonance imaging ("MRI"), ultrasound ("US"), and positron emission tomography ("PET")). In some cases, techniques are used for the planning and delivery of radiation therapy. For example, a method of treating a moving target, such as a tumor of a lung, can include "gating," or delivering radiation only when the target is within a specified window of trajectory. This method is inefficient because the target is only being irradiated for periodic intervals of time.

Another method of treating a moving target is referred to as breathing synchronized delivery ("BSD"). This technique utilizes an anticipated track, or path of motion, for a target to follow during treatment. To do so, a plan is developed that assumes the target will remain on the anticipated track, which has an anticipated period and phase throughout the entire treatment plan. Audio and visual guidance can be used to prompt a patient to follow the rigidly defined track. However, following a strictly defined pattern may be difficult for a large portion of radiation therapy patients.

SUMMARY

Radiation can be delivered to a moving region of interest (e.g., a target) without relying upon a priori knowledge of the region's location, period, and phase. Dynamic switching between a plurality of plans, or developing plans "on the fly" can be used to reflect changes in a patient's anatomical motion and apply a radiation treatment more effectively.

In one embodiment, the invention provides a method of delivering radiation therapy to a moving target. The method comprises the acts of generating a plurality of treatment plans, acquiring data related to movement of the target, determining which treatment plan corresponds to the data, and delivering the selected treatment plan.

In another embodiment, the invention provides a method of delivering radiation therapy to a moving target. The method comprises the acts of generating a plurality of treatment plans, acquiring data related to movement of the target, selecting a treatment plan that corresponds to a portion of the data, and switching between the selected treatment plans as the portion of the data changes.

In another embodiment, the invention provides a method of delivering radiation therapy to a patient when a region of interest is moving. The method comprises the acts of generating a plurality of treatment plans for delivering radiation therapy, delivering radiation therapy to the patient by following one of the plurality of treatment plans, monitoring the patient during the delivering radiation therapy, and changing to another treatment plan during the delivering radiation therapy based at least in part on the monitoring the patient.

In another embodiment the invention provides a method of delivering radiation therapy to a patient when a region of interest is moving. The radiation therapy is delivered by a radiation therapy system having a multi-leaf collimator. The method comprises the acts of generating a treatment plan for delivering radiation therapy, delivering radiation therapy to the patient by following the treatment plan, monitoring the patient during the delivering radiation therapy, and changing a leaf pattern of the multi-leaf collimator during the delivering radiation therapy based at least in part on the monitoring the patient.

In another embodiment, the invention provides a method of delivering radiation therapy to a patient when a region of interest is moving. The method comprises the acts of generating a treatment plan for delivering radiation therapy, delivering radiation therapy to the patient by following the treatment plan, monitoring the patient during the delivering radiation therapy, and changing a treatment parameter during the delivering radiation therapy based at least in part on the monitoring the patient.

Other aspects of the invention will become apparent by consideration of the detailed description and accompanying drawings.

DETAILED DESCRIPTION

Figure 1:
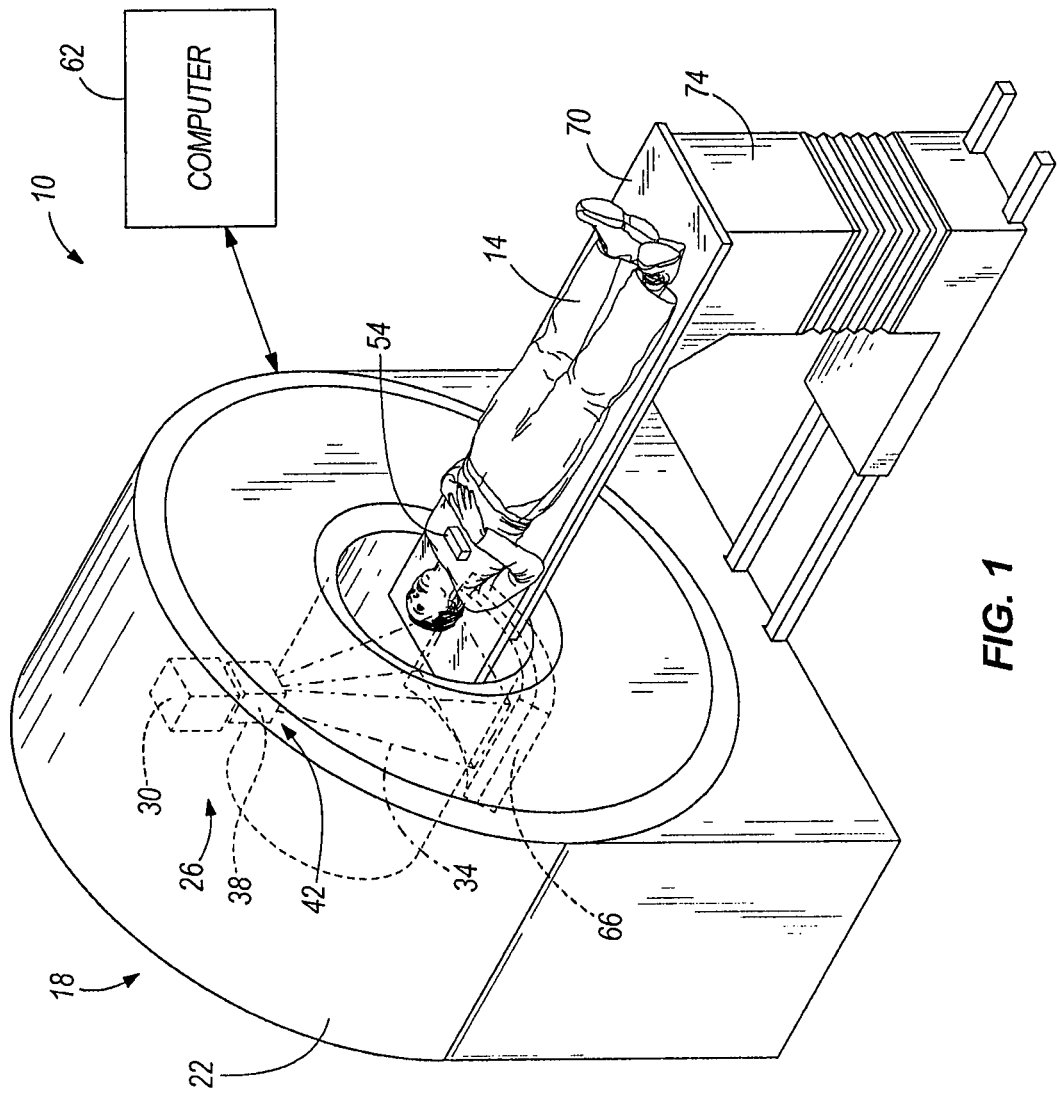
FIG. 1 is a partial perspective view, partial schematic illustration of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof herein are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a radiation therapy device 18 having a gantry 22. Though the gantry 22 shown in the drawings is a ring gantry, i.e., it extends through a full 360° arc to create a complete ring or circle, other types of mounting arrangements may also be employed. For example, a C-type, partial ring gantry, or robotic arm could be used.

The gantry 22 can support a radiation module, having a radiation source 26 and a linear accelerator 30 operable to generate a beam 34 of photon radiation. The radiation module can also include a modulation device 42 operable to modify or modulate the radiation beam 34. The modulation device 42 provides the modulation of the radiation beam 34 and directs the radiation beam 34 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target or target region (shown as 54), is an example of a region of interest. Another type of region of interest is a region at risk. If a portion includes a region at risk, the radiation beam is preferably diverted from the region at risk. The patient 14 may have more than one target region 54 that needs to receive radiation therapy. Such modulation is sometimes referred to as intensity modulated radiation therapy ("IMRT").

Other frameworks capable of positioning the radiation module at various rotational and/or axial positions relative to the patient 14 may also be employed. In addition, the radiation module may travel in path that does not follow the shape of the gantry 22. For example, the radiation module may travel in a non-circular path even though the illustrated gantry 22 is generally circular-shaped.

Figure 2:
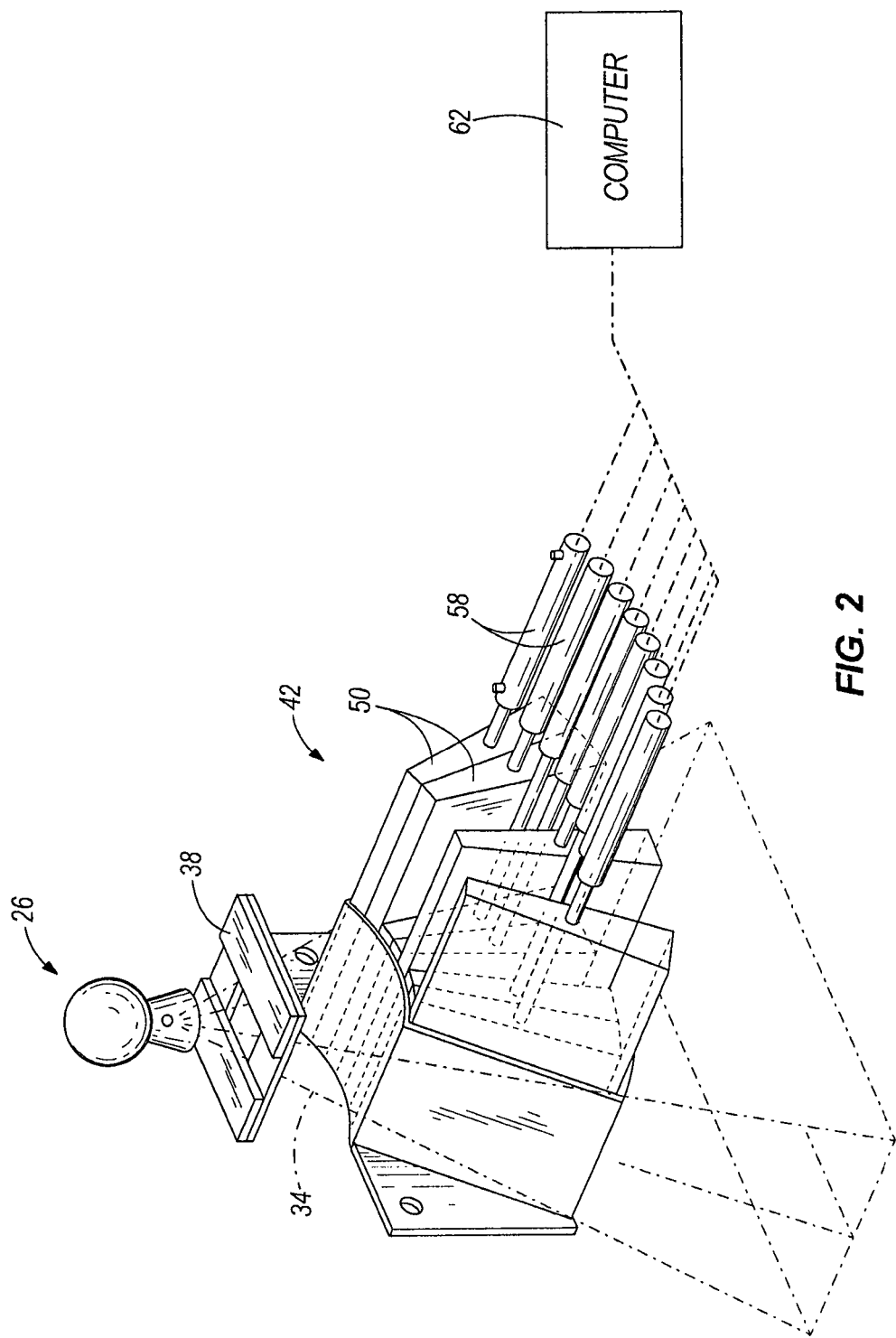
FIG. 2 is a partial perspective view, partial schematic illustration of a multi-leaf collimator that can be used in the radiation therapy treatment system illustrated in FIG. 1.

In one construction, and illustrated in FIG. 2, the modulation device 42 includes a collimation device. The collimation device includes the primary collimator 38 having a set of jaws. The jaws define and adjust the size of an aperture through which the radiation beam may pass. The collimation device further includes a multi-leaf collimator (MLC), which includes a plurality of interlaced leaves 50 operable to move from position to position, to provide intensity modulation. It is also noted that the leaves 50 can be moved to a position anywhere between a minimally and maximally-open position. The plurality of interlaced leaves 50 modulate the strength, size, and shape of the radiation beam 34 before the radiation beam 34 reaches the target 54 on the patient 14. Each of the leaves 50 is independently controlled by an actuator 58, such as a motor or an air valve, so that the leaf 50 can open and close quickly to permit or block the passage of radiation. The actuators 58 can be controlled by a computer 62 and/or controller.

The radiation therapy treatment system 10 can also include a detector 66, e.g., a kilovoltage or a megavoltage detector, operable to receive a radiation beam from the radiation module or from a separate radiation source. The radiation module and the detector 66 can potentially operate as a computed tomography (CT) system to generate CT images of the patient 14. The radiation module emits the radiation beam 34 toward the target 54 in the patient 14. The CT images can be acquired with a radiation beam 34 that has a fan-shaped geometry, a multi-slice geometry, or a cone-beam geometry. In addition, the CT images can be acquired with the linear accelerator 30 delivering megavoltage energies or kilovoltage energies. The target 54 and surrounding tissues absorb some of the radiation.

The radiation therapy treatment system 10 can also include a patient support, such as a couch 70 (illustrated in FIG. 1), which supports the patient 14. The couch 70 moves along at least one axis in the x, y, or z directions. In other constructions, the patient support can be a device that is adapted to support any portion of the patient's body, and is not limited to having to support the entire patient's body. The system 10 also can include a drive system 74 operable to manipulate the position of the couch 70. The drive system 74 can be controlled by the computer 62.

The computer 62 includes an operating system for running various software programs and/or communication applications. In particular, the computer 62 can include a software program 78 operable to communicate with the radiation therapy device 18. The computer 62 can include any suitable input/output device adapted to be accessed by medical personnel. The computer 62 can include hardware such as a processor, I/O interfaces, and storage devices or memory. The computer 62 can also include input devices such as a keyboard and a mouse. The computer 62 can further include output devices, such as a monitor. In addition, the computer 62 can include peripherals, such as a printer and a scanner.

Figure 3:
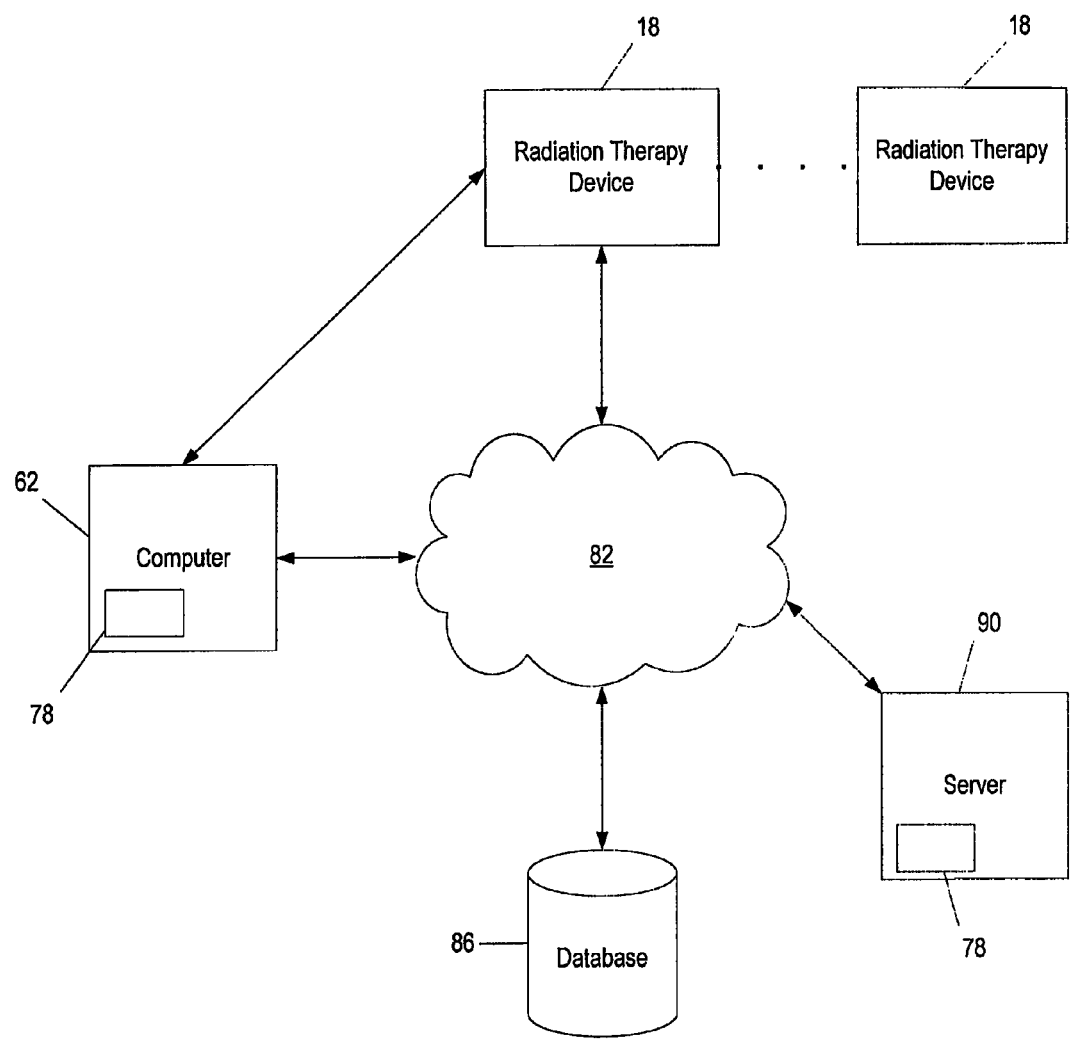
FIG. 3 is a schematic illustration of the radiation therapy treatment system of FIG. 1.

The radiation therapy device 18 communicates directly with the computer 62, and/or via a network 82, as illustrated in FIG. 3. The radiation therapy device 18 also can communicate with other radiation therapy devices 18 via the network 82. Likewise, the computer 62 of each radiation therapy device 18 can communicate with a computer 62 of another radiation therapy device 18. The computers 62 and radiation therapy devices 18 can also communicate with a database 86 and a server 90. A plurality of databases 86 and servers 90 can also communicate with the network 82. It is noted that the software program 78 could also reside on the server 90.

The network 82 can be built according to any networking technology or topology or combinations of technologies and topologies and can include multiple sub-networks. Connections between the computers 62 and device 18 shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers 62 and device 18 shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers 62 and radiation therapy devices 18 shown in FIG. 3 can also occur through the Digital Imaging and Communications in Medicine ("DICOM") protocol with any version and/or other required protocol. DICOM is an international communications standard developed by the National Electrical Manufacturers Association ("NEMA"), which defines the format used to transfer medical image-related data between different pieces of medical equipment. DICOM RT refers to the standards that are specific to radiation therapy data.

The two-way arrows in FIG. 3 generally represent two-way communication and information transfer between the network 82 and any one of the computers 62, the radiation therapy devices 18, and other components shown in FIG. 3. However, for some medical equipment, only one-way communication and information transfer may be necessary.

The multi-leaf collimator, as described above, can provide intensity modulation of the radiation beam 34 to accommodate varying conditions and regions of interest. More specifically, the intensity of the radiation beam 34 can be increased or decreased by moving the leaves 50 of the multi-leaf collimator 46. However, a target 54 that is in motion (e.g., a tumor of a lung, a heart, a digestive track, etc.) is difficult to treat with a continuous beam 34 because it does not often move in a repeated pattern.

Figure 4:
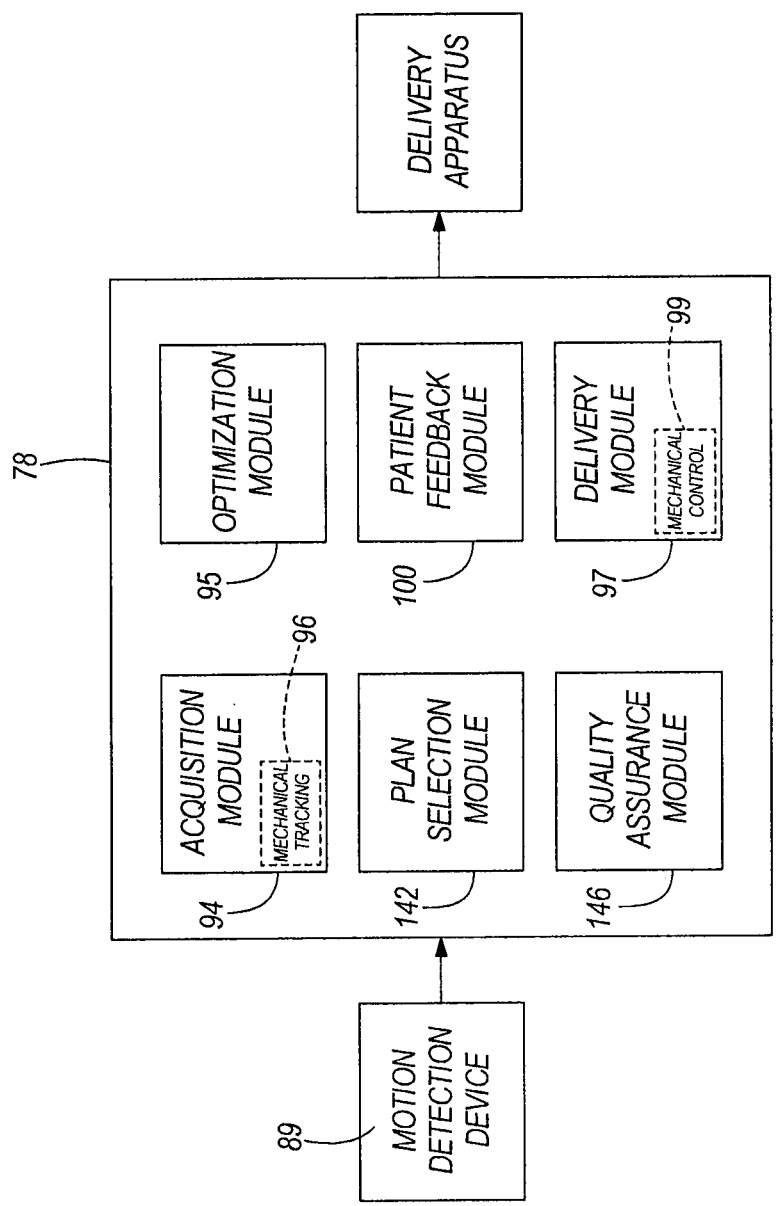
FIG. 4 is a block diagram of a software program that can be used in the radiation therapy treatment system of FIG. 1.

The software program 78 can accommodate a moving region of interest by varying the amount of radiation that is delivered to the patient 14 in accordance with the actual movement of the region of interest, as described below. An exemplary software program 78 is schematically illustrated in FIG. 4 according to one embodiment of the invention. The software program presents a class of solutions for delivering radiation to a region of interest without relying upon a priori knowledge of the location, period, and phase of the region of interest. One method utilizes the pre-generation of a family of delivery plans, and the dynamic switching between the plans to reflect changes in a patient's anatomical motion.

Figure 7:
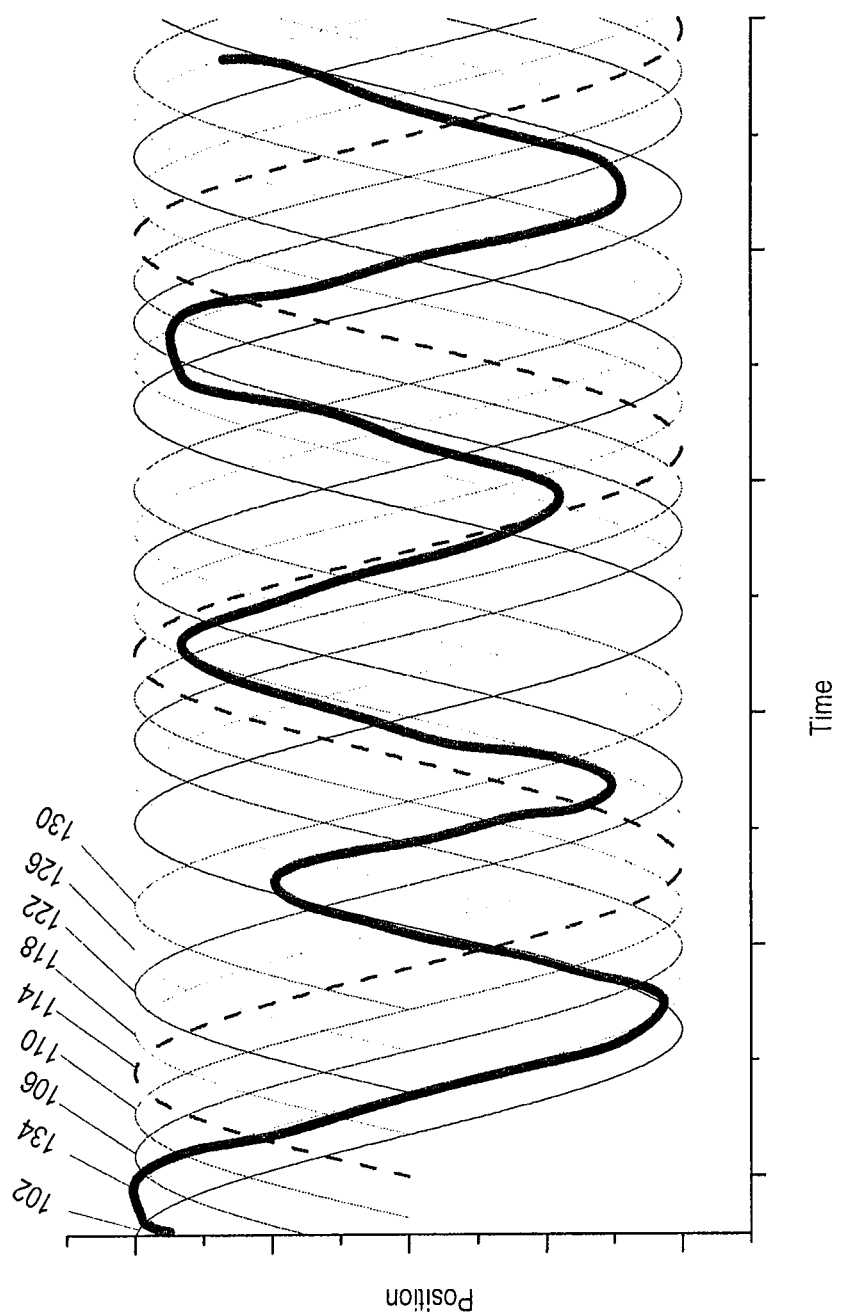
FIG. 7 is a graphical representation of a plurality of motion tracks and a representation of a patient's motion track.

One implementation is to begin by optimizing a BSD-type treatment, which assumes a target trajectory, breathing phase, and period throughout the treatment. However, in addition to optimizing that one plan, an additional set of plans can be optimized, each potentially with a different period, breathing phase, or other parameter varying with respect to the base BSD plan. Then, during treatment the patient begins by attempting to follow the target trace indicated in the BSD plan. However, if the patient's breathing deviates from this plan by more than a specified threshold, then the plan automatically switches to one of the alternate plans better matching the current region parameters. The delivery for an arbitrary patient breathing trace is illustrated by the thick line in FIG. 7. Thus, one benefit of this method is the enabling of a BSD-quality delivery with automatic error correction, and reduced motion-reproducibility requirements imposed on the patient.

In another implementation, rather than following a base four-dimensional ("4D") plan, the plans automatically switch as the patient breathes freely through the delivery. If desired, particularly erratic breathing, such as coughing, can be identified and the treatment may temporarily delay until the breathing again falls within specified tolerances. Similarly, if there are phases of breathing or regions of motion where the position of the region of interest is not well-defined, then treatment could be intentionally avoided during those phases. Such a decision may be made during planning, but can also be made dynamically, based upon perceived changes in the patient's anatomy of physiology.

A series of plans is generated with different possible criteria. All the plans, or many possible combinations of them, are maintained on the system 10 to be delivered whenever necessary. The breathing pattern is evaluated by an adequate evaluation device and based on real time decisions, potentially in conjunction with prior evaluation, based upon anticipated breathing scenarios. The system 10 evaluates and selects a plan or plan combination to be delivered. The selected plan can be accumulated with the previous fractions or part of the treatment previously delivered. As the plan is delivered, information can be recorded (or used for instance in conjunction with real time dose reconstruction) and potentially used to refine any plans for delivering future radiation (either during the current session or future sessions).

FIG. 4 discloses various modules that can be used with the software program 78. The modules include an optimization module 95, a plan selection module 142, an acquisition module 94, a delivery module 97, a patient feedback module 100, and a quality assurance module 146. Various implementations for the modules are described below. However, it should be understood that not all of the modules are required in all constructions of the system 10, and other modules not shown in FIG. 4 can be used with the software program 78. It should also be apparent that the modules can be combined into a lesser number of modules shown, that each module can include additional material not disclosed in the description herein, and that the names of the modules are for ease of description.

A. Optimization Module

One method for optimization, as mentioned above, is to optimize sets of 4D plans, each representing a different phase of motion (or period, etc.) Breathing cycles can be described and/or approximated by an infinite or finite Fourier expansion. In one possible implementation of the optimization module 95, a particular breathing cycle is described as a function of time of a linear combination of sine and cosine type functions having different frequency, amplitude, phases, etc. that evolves on time (See, e.g., FIG. 7). Under this condition, the optimization module 95 generates a set of plans, each of which represent an acceptable plan for delivery at a particular time. By having the plans or combinations of plans available, deliveries for more complex "regular" or "irregular" breathing patterns can be generated.

In another implementation of the optimization module 95, the plans need not each represent a complete 4D plan for a given parameter (e.g. period or trajectory), but the set of plans each represent a static delivery appropriate for a single phase of the motion cycle. The plans would automatically switch as the region of interest moves through its different motion phases. It is similarly possible to interpolate between phases in order to generate more images, optimize a larger number of phase-plans, and/or select a phase-specific plan.

Furthermore, it is possible to have multiple plans available for any given phase or set of parameters that utilize different optimization criteria. For example, rather than optimizing just one plan for each breathing phase, it is possible to optimize multiple sets of plans. This might entail having one plan for each breathing phase with a tight margin, and other plans for each breathing phase with wider margins (or with other constraints changing). As the treatment proceeds, the plan can be dynamically chosen based both on the region's of interest position, period, and/or phase, but also based upon its speed, uncertainty, and/or deformation. In cases where the target 54 is well-defined, plans from the narrow-margin set may be dynamically selected; whereas in cases of less certainty, larger margin plans may be selected.

One method of optimizing doses across multiple phase images is for the optimization module 95 to calculate dose beamlets for each phase, and then deform the beamlets in accordance with image deformation maps that relate the images. Although this method can be applied, it is not necessary, as doses can be calculated for each phase, and then added using deformation, such that deformation-adjusted beamlets are not required.

B. Plan Selection Module

The method for selecting the plan can be based upon a number of possible criteria. In one implementation of the plan selection module 142, the plan is based on criteria discussed above, such as the region's of interest position, period, and/or phase, each of which can be acquired by a motion detection device 89 and the acquisition module 94. Likewise, uncertainty and/or anatomical information can also be incorporated. The measurements are obtained from an applicable device, such as, but not limited to, camera systems, laser systems, X-Ray or fluoro systems, CT, MRI, PET, single photon emission computed tomography ("SPECT"), on-line CT, cone-beam CT, implanted markers, radiofrequency ("RF") localizers, ultrasound, breathing belts or cuffs, implanted X-Ray sources, acoustic sensors, strain gauges, RF emitters, and electrode based impedance measurements.

In another implementation, the plan selection module 142 selects plans based upon dosimetric characteristics. More specifically, a desired dose distribution is defined for each optimized plan section. Then during treatment, the plan selection module 142 determines which of the available plans would best match the planned dose given the patient's current anatomy and target information. This calculation can involve real-time dose calculations, but can be approximated by simplified or pre-computed calculations.

In yet another implementation, the plan selection module incorporates deformation with pre-computed calculations. This implementation relates dose in physical space to dose in specific tissues/targets. By incorporating deformation, it is easier to select plans that match the intended dose distributions in specific regions. Example deformation techniques and calculations are described in U.S. Provisional Patent Application No. 60/701,580; filed Jul. 22, 2005; titled SYSTEM AND METHOD FOR FEEDBACK GUIDED QUALITY ASSURANCE AND ADAPTATIONS TO RADIATION THERAPY TREATMENT, the entire content of which is incorporated herein by reference.

In another implementation that may also entail deformation, the desired dose is not only attempted to match the planned dose, but the plan selection module 142 simultaneously seeks to remedy any dose discrepancies from previous fractions or earlier in the fraction being delivered.

In another implementation of the plan selection module 142, the dynamic plan selection is not based solely upon matching the dose distribution (or cumulative dose distribution, deformed dose distribution, or deformed cumulative dose distribution), but also uses other criteria, such as target dose, sensitive structure dose, or dose-volume histograms ("DVHs"). Similarly, the plan selection is also based upon achieving a given biological outcome. And in this implementation, biological estimators are incorporated into the dose accumulation and/or plan selection process. The plan selection module 142 can also incorporate biological and clinical feedback regarding the patient, to facilitate the use of more aggressive plans in regions, times, or patients, where these plans might be better tolerated, and more conservative plans in more sensitive locations, times, or patients.

The dynamic plan selection of the plan selection module also need not be based solely on the patient's current information, but can use past information to account for lags in measurement and deliver a plan with appropriate anticipation of anatomical changes and compensating for delays in measurement and processing.

In another implementation of the software program 78, some or all of the dynamically selectable plans are not optimized in advance. With a fast optimizer, some of these plans are generated during the application of radiation therapy. Similarly, existing plans are modified during the application of radiation therapy to reflect physiological or anatomical changes. In other words, the optimization module 95 and the plan selection module 142 can closely interact (or be integrated) to provide a fast optimizer and selection module.

C. Acquisition Module Including a Mechanical Tracking Sub-Module

The tracking of the patient's breathing phase or motion status can be performed with many of the numerous motion detection devices and related acquisition software for tracking patient physiology. The acquisition module 94 can include a motion or mechanical tracking sub-module 96. Example motion detection devices include, but not limited to, spirometers, camera systems, stereoscopic cameras, laser systems, fluoroscopy, X-Ray systems, CT, implanted markers, RF markers, MRI, strain gauges, and electrode impedance measurements.

In one implementation of the acquisition module 94, instead of or addition to the just-describe tracking methods, the tracking is also performed with data collected during the delivery, such as through a megavoltage CT, a kilovoltage CT, or a cone-beam CT system. The mechanical tracking module 96 processes the data from these systems to identify the location, phase, and position of the region of interest, and also the patient's breathing phase and anatomical changes. The information is extracted either from the reconstructed images, from the projection data, or from a hybrid of reconstructions and projection data. This implementation may also incorporate a priori information from previous or generic images or projection data sets.

For example, a 4D model of tumor trajectory is established from the planning images, and this model is verified with the projection data, as well as identifying the patient's present breathing phase. Sinograms are checked for the presence and location of the structures or markers of interest. This information identifies the current or recent patient breathing phases, the location of the tumor, whether the tumor is off any predicted geographic or temporal track and what other plans might be useful for delivering dose in the present or future anatomy. This information can also be used to detect locations, via magnification, in single or orthogonal portal/CT projections.

In another implementation, the mechanical tracking sub-module 96 uses the information to analyze various delays (measuring position, measuring couch, etc.) that can be accounted for in the plan selection. This information can also verify that an anticipated target 54 (or region of interest) trajectory remains valid, and can distinguish low-frequency (base motion) from high-frequency (noise, irregularities) to estimate appropriate amounts of compensation. In some implementations of the mechanical tracking sub-module 96, the compensation is partially achieved through dynamic couch corrections.

When using transmitted radiation for detection of phase and/or position, it is preferable to minimize unnecessary radiation. For this reason, one implementation of the acquisition module 94 uses the radiation being delivered as part of the treatment. The data is generally limited in scope, as the treatments are typically intended only to deliver radiation to target regions 54. However, the amount of obtained data may be adequate for identifying the necessary features, positions, or phases of the region of interest.

In another implementation, the acquisition module 94 acquires additional information obtained from briefly "flashing" additional MLC leaves open to create transmission data for a larger region of the patient. This can be done more often, or with a larger number of leaves, when more data is needed; or it can be done less frequently, or with fewer leaves, providing less information, but sparing dose and verifying as necessary. When using fewer leaves, or reduced frequency, it may be that localizations are better known, other devices are also being used, the treatment quality is less dependent on the changes being verified, or for other reasons.

The principle of reduced dose can also be applied to imaging systems without MLCs attached. For example, if an additional source (such as an X-Ray source) and a detector are being used for verification, it is known in the art that such a system is used to track motion, and phase in some cases, by running the system in fluoroscopic mode. However, this contributes a very high dose to the patient. Thus, in another implementation, the mechanical tracking sub-module 96 detects and verifies phase and/or position information with a very slow or discrete fluoroscopy use, as opposed to continuous use. For example, rather than using continuous tracking, fluoroscopy frames are taken at specific times to determine or corroborate a target (or region of interest) position or phase. These times may be equally spaced, or they may be spaced based upon other patient feedback, or spaced based on anticipated motion phases or locations. As such, this implementation can be used for independent measurement, or can be used to corroborate external or surrogate-based verification devices with low-dose internal images.

1. Real-Time Respiratory Motion Monitoring Via Intensity Modulated Radiation Therapy ("IMRT")

Real time tracking of tumor position or monitoring motion of internal organs is important for extending radiation therapy from three dimensional ("3D") to four dimensional ("4D").

All 4D radiotherapy techniques, whether based on gating, tracking, BSD, or the free-breathing delivery ("FBD") technique, require the real time knowledge of the breathing states, or at least the tumor position. Some available respiratory monitoring techniques include marker methods and airflow methods. Both methods indirectly monitor respiratory motion by some kind of surrogate. The marker methods use external or internal markers as the surrogate. Cameras (for external markers) or fluoroscopy devices (for internal markers) are used to track these markers. The airflow methods use a pyrometer to measure the airflow during breathing, and the airflow is used as the surrogate for respiratory motion. The disadvantages of these surrogate methods include: 1) how well the surrogate correlates to the internal respiratory motion and what kind of correlation are doubtful; 2) the respiratory motion is a complicated 4D deformation process, therefore, a surrogate with one or few parameters have very limited representation for the respiratory motion of a large body section; and 3) there exist (potentially unstable) delays between the surrogate and the respiratory motion.

One alternative method includes a direct method to monitor the respiratory motion. The method directly monitors the internal organ motion with respect to the treatment beam. The method can be implemented directly in the system 10 with a detector system. An example of a detector system is the HI-ART brand radiation therapy system offered by Tomo-Therapy, Inc. with a web site at www.tomotherapy.com. No additional devices, such as a camera, a spirometer, or a fluoroscopy device, are required. No extra radiation is necessary.

For example, a radiation therapy treatment system may have a complete set of 3D images, each 3D image being a snapshot of the patient at certain breathing states (or phases). A planning fluence map (or sinogram) is typically available before the treatment. Based on a 3D representation of the patient, for each projection (line) of the planning sinogram, the computer 62 calculates the detector response (output signal) by direct ray tracing or Monte-Carlo simulation. Therefore, for all N phases of the 4D image, the system precalculates N output signals for each projection. After doing the precalculation, the monitoring of respiratory motion is straightforward. The system need only to compare the real detector signal with the precalculated N detector signals, the one with the largest similarity measure gives the breathing phase at that time. A simple correlation could be used as the similarity measure. The correlation can be defined as:

$$c_i = \frac{2(s_i - \bar{s})(s - \bar{s})}{\|s_i - \bar{s}\|^2 + \|s - \bar{s}\|^2}; \qquad [e1]$$

where
  $s_i$ is the precalculated detected signal corresponding to the $i^{th}$ phase,
  s is the measured detected signal,
  $\bar{s}$ is the mean of N phase detector signals $$\bar{s} = \frac{1}{N}\sum_{i=1}^{N} s_i,$$

and
  wherein the detector signal states for a vector of the signals from all detectors.

D. Delivery Module Including a Mechanical Control Sub-Module

In some constructions, mechanical methods can be used for correcting the free-breathing techniques described above, or used with conventional plans (e.g. static plans, breath-hold plans, etc.). For example, the primary collimator 38 can follow the motion of the regions of interest along with the modulation device 42 modulating the beam. As another example, the couch 70 can be used to facilitate dynamic repositioning.

In one construction, the mechanical tracking module 96 continuously determines the patient phase throughout the delivery. The offset of any relevant structures from the planning position is determined by a mechanical control sub-module 99 of the delivery module 97. The sub-module 99 decomposes the offset into a transversal component and a longitudinal component. A target 54 affected by motions on the inferior-superior direction during treatment (the more common) is accounted by moving the primary collimator 38. The primary collimator 38 can include a set of jaws before the modulation device 42. The jaws define and adjust the size of an aperture through which the radiation beam may pass. Alternatively, a segmented primary collimation allows creating shapes that follow the target 54 and the beam is modulated by the modulation device 42. Couch motion can also be used in combination to either create other motions or extend the degree of motion.

A difference with other mechanical techniques to correct motion is that the one presented here does not use the modulation device 42 to account for motion on the inferior-superior direction. The primary collimator 38 is used to follow the motion on this direction, alone or in combination with the couch 70. One of the advantages is that, in principle, no plan changes are necessary to correct for this motion (except for a few adjustments on the output for different directions). However, this technique can also be incorporated into the dynamic plan modification or switching methods described herein. In addition, dynamic plans can be optimized for different collimator positions to incorporate any beam changes relevant to the different jaw locations. In another implementation, the mechanical control sub-module 99 models changes without separate plans.

Corrections for motions in other (non inferior-superior) directions can also be accounted for. Corrections in the beam direction are corrected either with the couch 70 or by a simple change of the MLC modulation time accounted for inverse square corrections. Couch motion can also be used to account for this motion alone or in conjunction with MLC time changes.

Motions on the plane perpendicular to the beam (i.e., not the inferior-superior direction) can be accounted for by either changing the leaf pattern or by a combination of leaf pattern and couch motion. It should be noted that mechanical motions, such as collimator motion, can be either incorporated into the planning process, or performed in response to detected motion. That is, in some cases, the collimator motion is pre-programmed based upon the anticipated patient breathing trace. Yet, either the collimator motion or plan is dynamically altered if the patient's motion does not follow the anticipated trace. In other cases, motion of the collimator 38 is a purely compensatory method for patient motion deviations. Under these conditions, the target 54 and sensitive structure motions are accounted for in real time. It is envisioned that changing the motion of the collimator 38 or changing the leaf pattern may result in a reordering of the treatment plan or scaling of the treatment plan.

E. Patient Feedback Module

Although various techniques described herein are designed to free a patient from the constraint of a required breathing pattern, this does not require that a patient breathe without any assistance from a guidance system, or without any "target" breathing traces. Instead, in some constructions of the system 100, even if a patient deviates from an intended breathing track, the treatment dynamically adjusts accordingly.

To this extent, a patient feedback module 100 can provide the patient with feedback on their motion control, and potentially guidance signals. This can be performed using a goggle system, a video projection inside or visible from the gantry (potentially visible through mirror glasses or an auxiliary device), audio feedback, or the like.

A patient feedback module 100 can also assist patient motion by having the patient willfully breathe under assistance by a respirator. A respirator helps standardize the patient on a more reproducible breathing pattern, but deviations would ideally still be handled through the use of multiple plans and dynamic plan switching. In some cases, it may also be that the patient's active breathing in conjunction with a ventilator are adequate to deliver a three-dimensional ("3D") plan.

F. Quality Assurance Module

Another aspect of some constructions of the system 10 is the provision of various techniques for quality assurance and verification. For example, one such technique for the quality assurance module 146 applicable to validation in phantoms is to develop plans that are intentionally different, such that the plan being delivered is readily determined with external measurement devices, such as ion chambers, scintillation fluid, film, thermoluminescent dosimeters ("TLDs"), diode detectors, flat-panel imagers, or other radiation detectors or monitors. Then by changing the motion-response curve, the system verifies how quickly and appropriately the plan change responds.

In another implementation, the quality assurance module 146 performs validation that can be applied to both patients and phantoms by dose recalculation in a 4D image set based upon the recorded motion trace from the treatment. The dose accumulated across the 4D images provides the net delivered dose, ideally adjusted for deformation. This dose is compared to doses measured at points inside, on, or separate from the patient to validate the net dosimetric effect and that both moving and non-moving regions are handled correctly. This aspect of 4D dose calculation based upon a measured motion pattern can likewise be applied to other deliveries besides the free-breathing adjusted deliveries described herein.

DETAILED EXAMPLES

Figure 5:
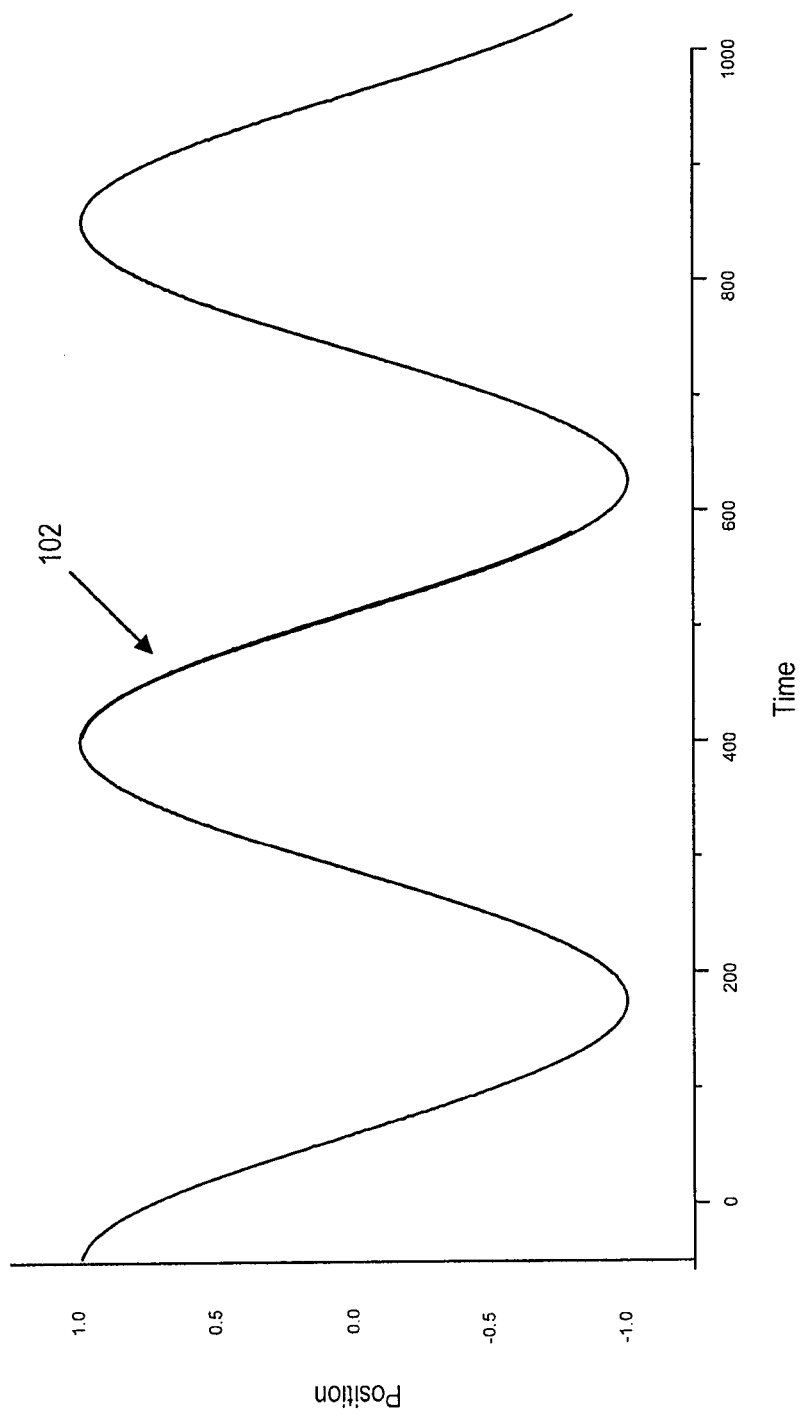
FIG. 5 is a graphical representation of a motion track.
Figure 8:
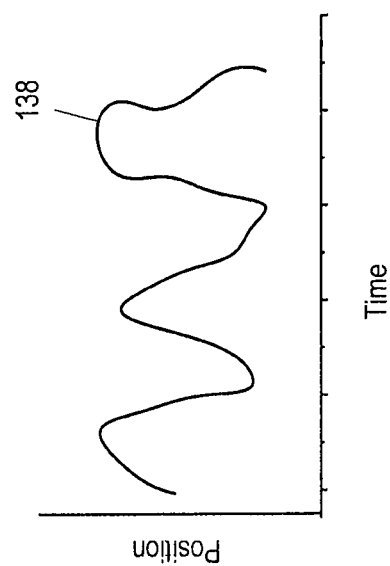
FIG. 8 is a graphical representation of a motion track.
Figure 6:
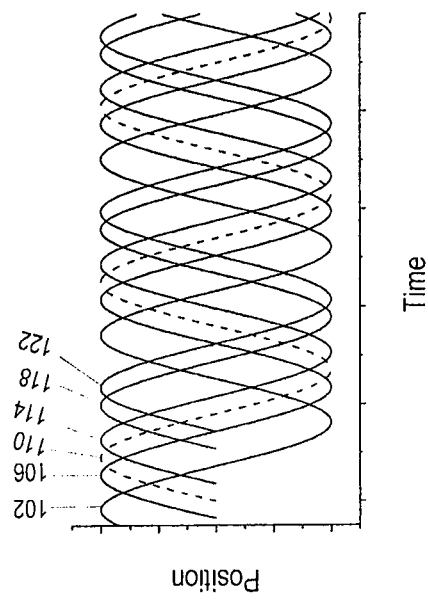
FIG. 6 is a graphical representation of a plurality of motion tracks.
Figure 9:
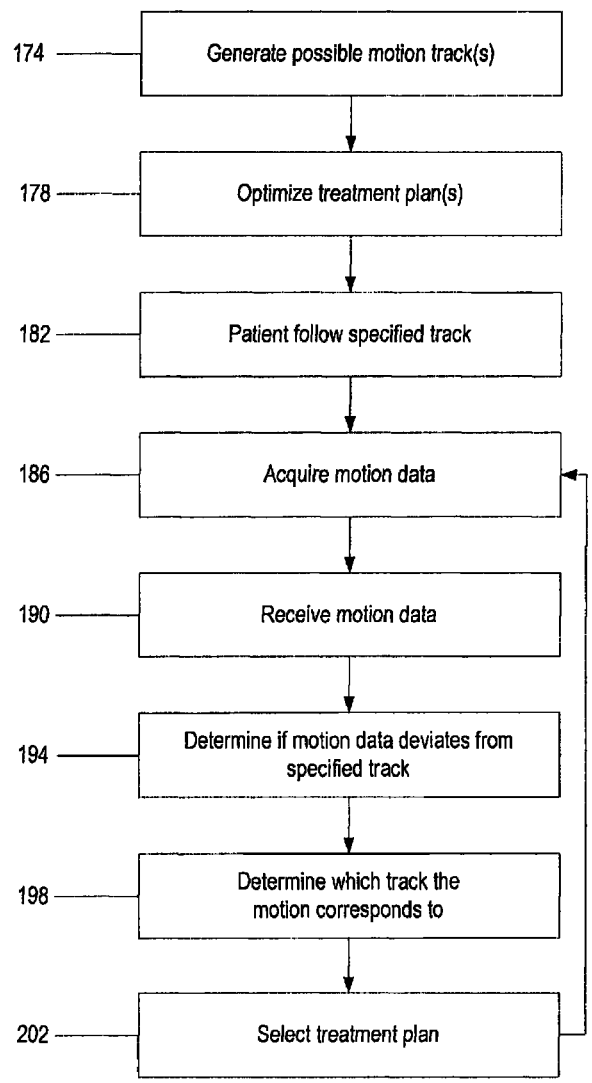
FIG. 9 is a flow chart of a method of delivering radiation therapy treatment to a moving region of interest according to one embodiment of the invention.

FIG. 9 illustrates a flow chart of a method of delivering radiation therapy to a moving region of interest according to one embodiment of the invention. The software program 78 generates (block 174) a plurality of tracks 102-130 (FIGS. 5 and 6) that represent anticipated motion (e.g., the patient's breathing pattern). The treatment plans are optimized (block 178) by the optimization module 95 to correspond to the tracks 102-130. For example, each treatment plan can be optimized to correspond to one of the tracks 102-130. As another example, a plurality of treatment plans can be optimized and then combined to correspond to one of the tracks 102-130. The patient 14 attempts (block 182) to follow one of the tracks 102-130. While the treatment is being delivered, the acquisition module 94 acquires (block 186) motion data, which relates to movement of the region of interest (e.g., target 54). The mechanical tracking module 96 receives (block 190) the motion data (shown as motion track 138) from the motion detection device 89. The plan selection module 142 determines (block 194) if the motion data deviates from the selected track that the patient 14 is following. The plan selection module 142 can compare the deviation to a range to determine if the deviation is greater than a specified threshold. The plan selection module 142 determines (block 198) which track 102-130 the motion most closely, presently corresponds. The plan selection module 142 selects (block 202) the treatment plan that corresponds to the identified track 102-130. The patient's treatment can include delivery of portions of a plurality of treatment plans as the selected plan can automatically switch to correspond to the patient's actual motion. This is best shown as line 134 of FIG. 7. As the line 134, changes to a different motion track 102-130, the corresponding plan is selected. Patient feedback can be provided to the patient from the patient feedback module 100 to promote a more consistent track 134.

Figure 10:
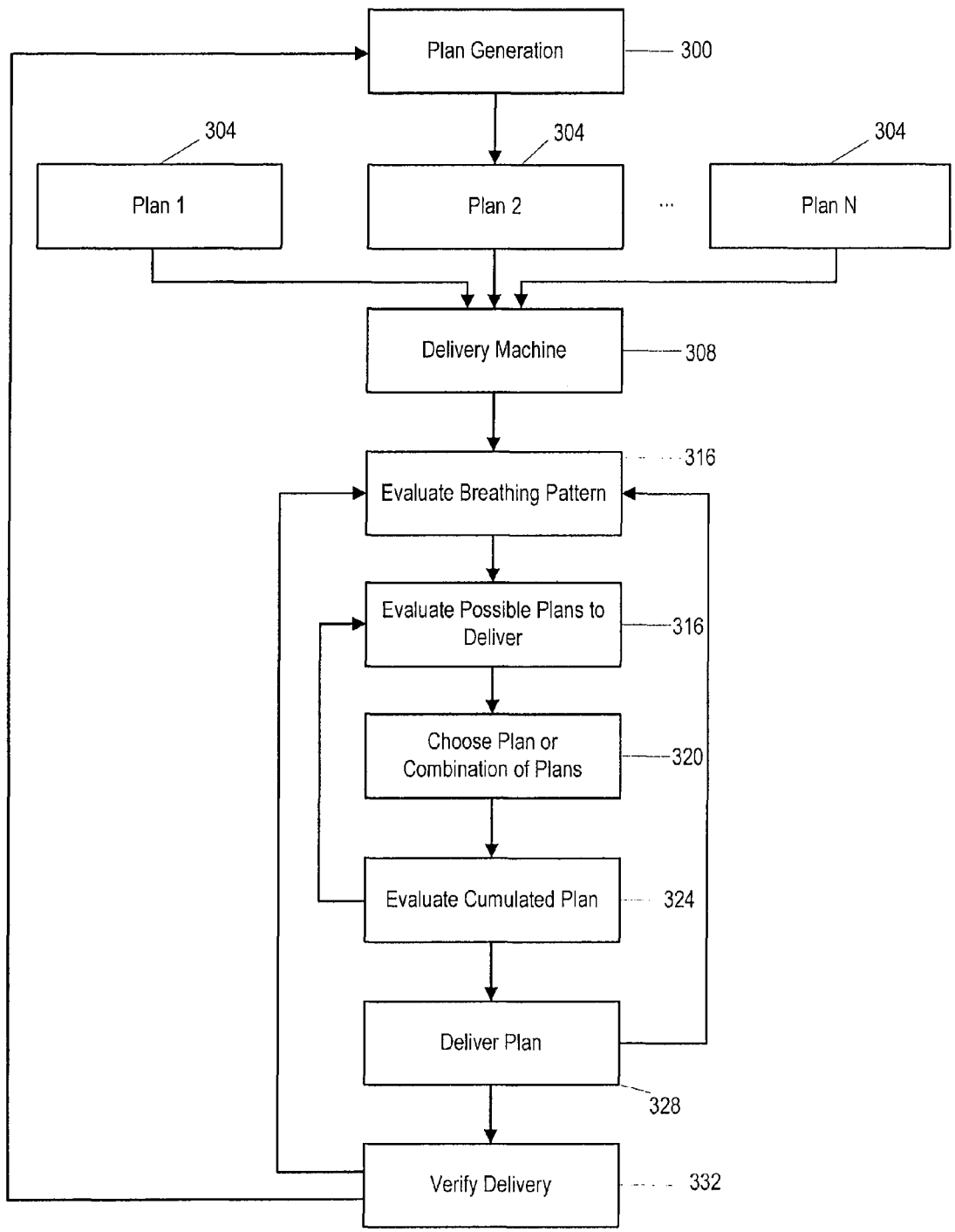
FIG. 10 is a flow chart of a method of delivering radiation therapy treatment to a moving region of interest according to one embodiment of the invention.

FIG. 10 illustrates a flow chart of processes that can be included in the administration of radiation therapy treatment. The process begins with plan generation (block 300). As described above, plans and phases can be determined using mathematical models, deformation models, and physiological models. After a plurality of plans (blocks 304) are generated, they can be loaded into the radiation therapy device 18 (block 308). More specifically, the plans can be loaded into the computer 62, which has the ability to control the components and operation of the radiation therapy device 18 (e.g., via the delivery module 97).

After the treatment plans have been stored in the radiation therapy device 18 (or computer 62), radiation therapy treatment of the patient 14 can begin. In the first stage of treatment, movement patterns are monitored and evaluated (block 312). As described above, the movement patterns can be measured using the movement detection devices 89 and the acquisition module 94, for example. After monitoring the patterns of motion, a list of potential treatment plans can be generated based on the motion pattern (block 316). A treatment plan can be evaluated according to the time and spatial relationships between the plan and the motion pattern of the patient 14. After the list of potential treatment plans is determined, a treatment plan or a combination of treatment plans can be selected (block 320). The treatment plans can be chosen automatically according to the computer 62, or manually by a doctor or other professional. The plan or combination of plans that most closely matches the motion of the region of interest is generally selected. After selecting a treatment plan, it can be evaluated (block 324). Evaluation parameters can include information relating to the position of the region of interest, the deformation of the region of interest, the dose being administered, or a combination thereof. In some embodiments, if the plan that is selected in block 320 is evaluated (e.g., by the quality assurance module 146) and it is not deemed to be an effective treatment, the process can return to block 316 to re-evaluate potential treatments plans to deliver.

If, however, the treatment plan is evaluated and it is projected to have the intended result, it can be delivered by the radiation therapy device 18 (block 328). During delivery of the plan, the process can return, and the subsequent acts can be repeated. In other implementations, after a plan is delivered it is verified (block 332). Delivery verification can be used to determine the dose of radiation that was actually delivered to the patient 14 as well as the deformation that occurred. As described above, the dose and deformation information can have an impact on which plans are subsequently implemented. After the delivery of the plan is verified, the process can return to the plan generation stage at block 300, and the process can be repeated. In other implementations, the process is returned to the motion evaluation block 312, and the remainder of the process is repeated.

1. Detailed Example

Delivery of Helical Coplanar IMRT Beams for Moving a Target

As previously stated, an example radiation therapy treatment system capable of incorporating the invention is the HI-ART brand radiation therapy treatment system offered by TomoTherapy, Inc. with a website at www.tomotherapy.com. The TOMOTHERAPY HI-ART brand system is an example of a helical radiation therapy treatment system, which is superior to a conventional IMRT in many aspects. The delivery of helical coplanar intensity modulated beams is one example advantage. In one embodiment, the helical delivery system typically has the following features: 1. fixed jaw width, 2. fixed jaw position and orientation, 3. constant couch speed, 4. constant gantry rotation speed, and 5) one dimensional (1D) binary MLCs for intensity modulation.

But on the other hand, such simplicity in the delivery system also posts some limitations in the situation of a moving region of interest (e.g., target motion results from respiratory motion). Conventional gating and tracking techniques for the moving region of interest may not be easily implemented in the helical system. For example, gating technique requires stopping gantry rotation or couch movement. The tracking technique requires real time jaw tilting. BSD is attractive if the patient follows the planned breathing pattern at all times. But it is hard for the helical system to correct any out-of-phase-breathing.

For one construction of a modified helical system, the system assumes the following: 1. the target position can be real time determined; 2. the target motion is rigid body motion, the deformation, if any, is negligible compared to the rigid body motion; and 3. the target motion within one projection is negligible. Assumption 1 is feasible through the combination of a 4D representation of the pre-treatment patient body (such as 4D CT), and real time phase determination techniques (such as using camera, spirometer or treatment beam as presented above). Assumption 2 is reasonable for most cases. This is also the basic assumption for the tracking technique used in conventional IMRT. Assumption 3 is actually the time resolution of some delivery systems, such as the HI-ART system provided by TomoTherapy, Inc.

The helical delivery, in some constructions, is projection-wised. Each projection is indicated by three parameters:

k is the rotation index (k is an integer number);

$\phi$ is the gantry angel ($\phi \in [0, 2\pi]$); and p is the MLC leaf index $$p \in \left[-\frac{P}{2}, \frac{P}{2}\right].$$

The pair (k,$\phi$) is composed of the projection index. The time t is linearly proportional to projection index t=t(k,$\phi$).

Let $\Delta Z$ be the couch proceeding per rotation. Then couch position is $$Z(k, \phi) = \left(k + \frac{\phi}{2\pi}\right)\Delta Z \qquad [e2]$$

Let $I=I(k,\phi,p)$ be the planning sinogram. The function value $I(k,\phi,p)$ represents the beam-on time for leaf p at projection $(k,\phi)$. The planning itself can be based on a static patient model (3D plan) or BSD model (4D plan).

Let $I'=I'(k,\phi,p)$ be the delivery sinogram. One objective of this subsection is to determine the $I'=I'(k,\phi,p)$ in case of the moving target.

Let:
$x=x(k,\phi)$: the planning target position at projection $(k,\phi)$. The planning itself can be based on static patient model (3D planning) or BSD model (4D planning). $x=(x,y,z)$.
$x'=x'(k,\phi)$: the delivery target position at projection $(k,\phi)$. This is determined according to assumption 1.
$u=u(k,\phi)=x'(k,\phi)-x(k,\phi)$: the target displacement between the delivery and the planning; $u=(u_x,u_y,u_z)$.

One can further decompose the transversal target displacement to a perpendicular-to-beam direction (parallel to MLC line) component $u_\perp$ and to a parallel-to-beam direction component $u_\parallel$. The result is:

$$u_\perp(k,\phi) = u_x(k,\phi)\cos\phi + u_y(k,\phi)\sin\phi \qquad [e3]$$

$$u_\parallel(k,\phi) = u_x(k,\phi)\sin\phi + u_y(k,\phi)\cos\phi \qquad [e4]$$

For the parallel-to-beam direction motion component $u_\square$, one needs inverse square correction and attenuation correction. Let the correction factor be r $$r(k,\phi) = r_1(k,\phi) r_2(k,\phi) \qquad [e5]$$

where $r_1(k,\phi)$ is inverse square correction. Let $s(k,\phi)$ be the planning source to target distance, $$r_1(k, \phi) = \frac{[s(k, \phi) + u_\parallel(k, \phi)]^2}{s(k, \phi)^2} \qquad [e6]$$

And let $r_2(k,\phi)$ be the attenuation correction:

$$r_2(k, \phi) = \frac{\exp\left(-\int_0^{s(k,\phi)} \mu \, dt\right)}{\exp\left(-\int_0^{s(k,\phi)+u_\parallel} \mu \, dt\right)} \qquad [e7]$$

Equation [e7] is feasible only if the system has 4D CT, otherwise, the system has to use some other approximations.

The in plane perpendicular-to-beam direction motion component $u_\perp$ is correctable by shifting the MLC pattern. That is $$p'(k,\phi) = p(k,\phi) + u_\perp(k,\phi) \qquad [e8]$$

To correct the z component motion, one needs to shift the projection. Also, one has to keep the same gantry angle as planning sinogram so that the RAR has the optimal spacing as planned. Therefore, we only need to change the rotation index k $$k' = k + \text{round}\left(\frac{u_z}{\Delta Z}\right) \qquad [e9]$$

$$\phi' = \phi \qquad [e10]$$

It is also possible that due to arbitrary motion pattern, several projections will map to the same projection and some projections are not mapped at all. One has to consider letting the maximum achievable beam on time for each projection be $I_{max}$, such that the delivery strategy for an arbitrary moving target 54 is as illustrated by following pseudo code.

```
Let I(k, φ, p) be the planning sinogram
While ∃(k, φ, p) such that I(k, φ, p) > 0
    ForEach rotation index k
        ForEach gantry φ
            Get planning target position x
            Determine real target position x'
            Calculate displacement u = x - x'
            Calculate u_∥ and u_⊥ as in [e3] to [e4]
            Calculate in plane parallel motion correction
            factor r as in [e5] to [e6]

Calculate k' = k + round(u_z/ΔZ)

ForEach MLC index p
                Calculate p' = p + u_⊥
                Calculate
                I'(k, φ, p) = min(I(k', φ, p'), I_max)
                Let  I(k, φ, p) = I(k, φ, p) − I'(k, φ, p)
                Apply
                correction   I'(k, φ, p) = rI'(k, φ, p)
                Deliver I'(k, φ, p)
            EndFor
        EndFor
    EndFor
EndWhile
```

Figure 11:
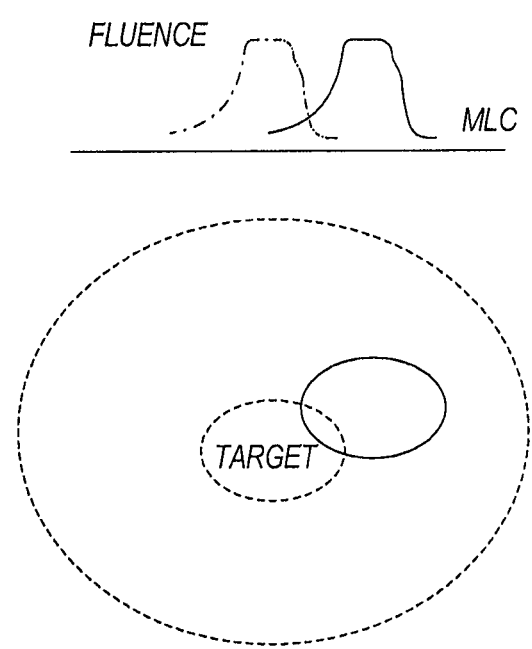
FIG. 11 is a graphical representation of a transversal motion correction.

FIG. 11 is a representation of a transversal motion correction. The dashed line is the planning target position and beam intensity, the solid line is the delivered target position and beam intensity.

Figure 12:
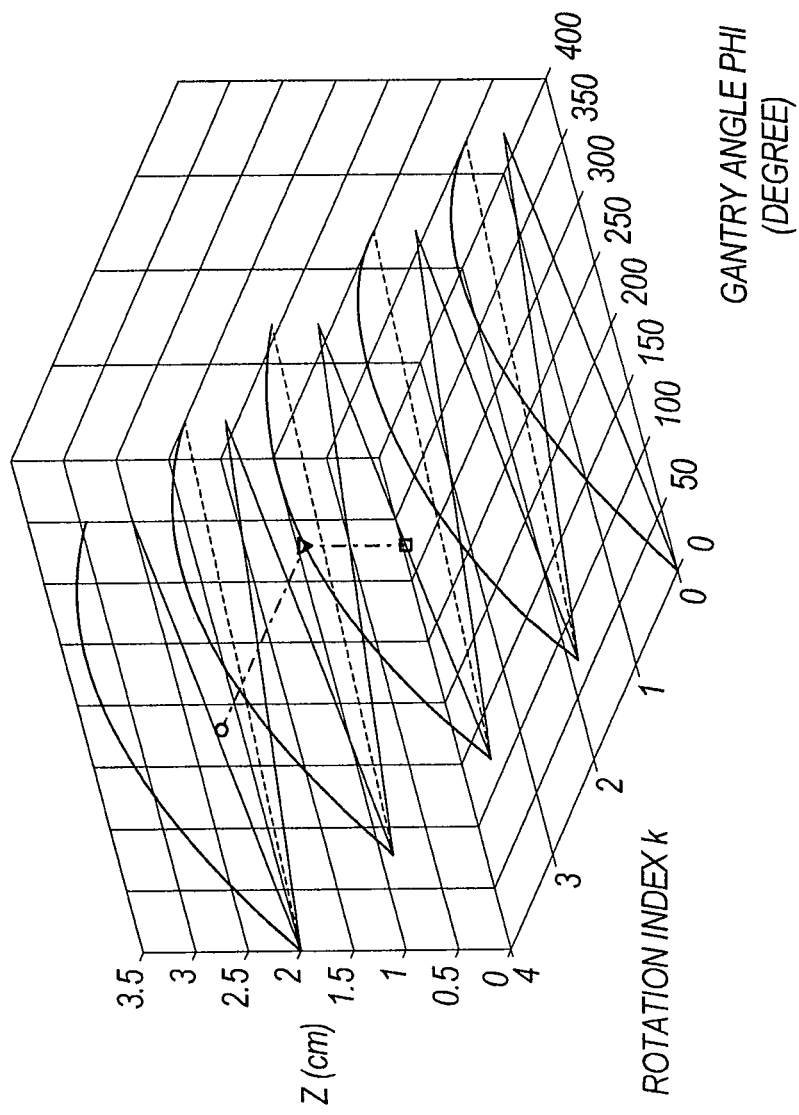
FIG. 12 is a graphical representation of a static plan in the case of a moving region of interest.

FIG. 12 is an illustration of a helical system delivering a static plan for a moving target 54. The solid line is the planning target position for each projection. The dashed line is the real target position during delivery. The square indicates the planed projection, and the triangle indicates the real target when the gantry and the couch are at that position. The circle indicates which projection needs to be delivered at that moment. The circle is usually located between two rotations. An interpolation method typically needs to be used to determine the beam intensity.

Figure 13:
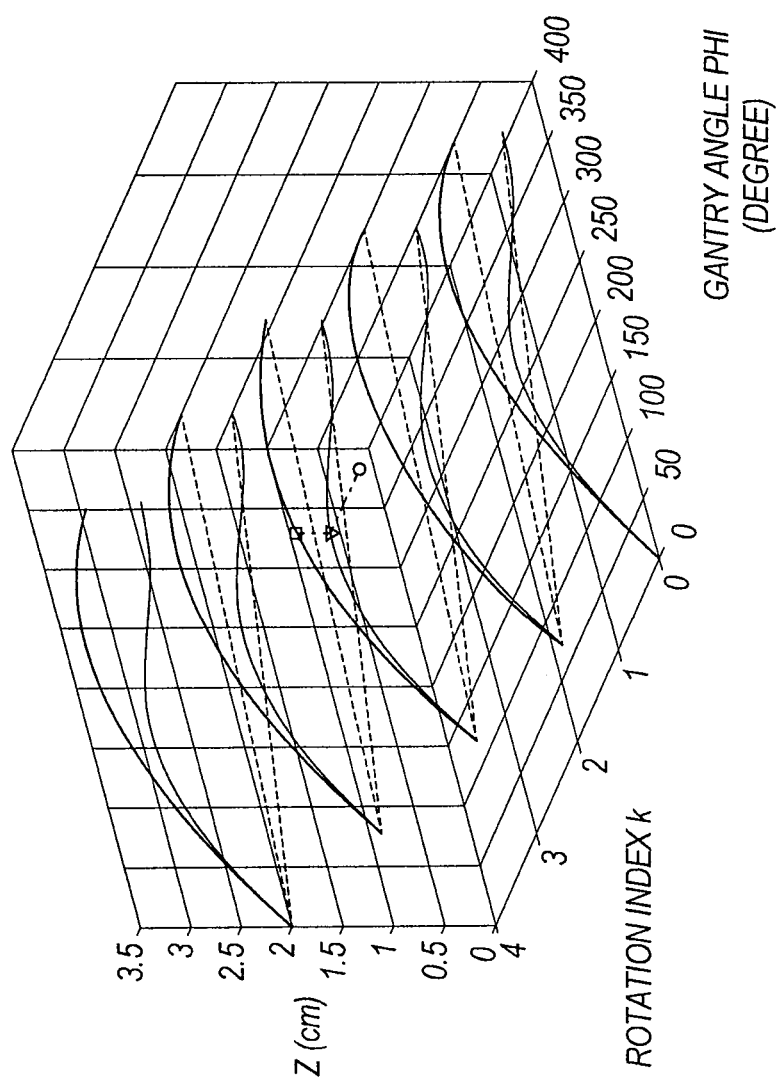
FIG. 13 is a graphical representation of a BSD plan in the case of a moving region of interest.

FIG. 13 is similar to FIG. 12, except that a certain pattern of breathing motion is planned (BSD plan, solid line), while the real target position (dashed line) is different from the BSD plan. The square indicates the planed projection, and the triangle indicates the real target when the gantry and the couch are at that position. The circle indicates which projection needs to be delivered at that moment. The circle is usually located between two rotations. An interpolation method needs to be used to determine the beam intensity.

Thus, the invention provides, among other things, new and useful systems and methods of delivering radiation therapy to a moving region of interest. Various features and advantages of the invention are set forth in the following claims.

The invention claimed is:

1. A method of delivering radiation therapy to a patient when a region of interest is moving, the radiation therapy being delivered by a radiation therapy system including a multi-leaf collimator, the method comprising:
generating a treatment plan for delivering radiation therapy, the treatment plan including a series of machine instructions;

activating a radiation beam for delivering radiation therapy to the patient by following the treatment plan;
monitoring the patient while the radiation beam is active and delivering radiation to the patient; and
changing a leaf pattern of the multi-leaf collimator from the leaf pattern as specified by the treatment plan while the radiation beam is active based at least in part on the monitoring the patient,
wherein the changing a leaf pattern includes reordering the machine instructions.

2. A method as set forth in claim 1 wherein changing a leaf pattern further includes scaling the treatment plan.

3. A method as set forth in claim 1 wherein the changing a leaf pattern includes dynamically optimizing the treatment plan.

4. A method as set forth in claim 1 wherein the changing a leaf pattern is further based on dosimetric information.

5. A method as set forth in claim 4 wherein the dosimetric information comprises at least one of an accumulated dose for a current session and an accumulated dose for all sessions.

6. A method as set forth in claim 4 wherein the changing a leaf pattern includes performing deformation with the treatment plan.

7. A method of delivering radiation therapy to a patient when a region of interest is moving, the radiation therapy being delivered by a radiation therapy system, the method comprising:
generating a treatment plan for delivering radiation therapy, the treatment plan including a series of machine instructions for controlling a multi-leaf collimator;
activating a radiation beam for delivering radiation therapy to the patient by following the treatment plan;
monitoring the patient while the radiation beam is active and delivering radiation to the patient; and
changing a treatment parameter while the radiation beam is active and delivering radiation to the patient based at least in part on the monitoring the patient,
wherein the changing a treatment parameter includes changing a leaf pattern of the multi-leaf collimator and scaling at least one of the machine instructions.

8. A method as set forth in claim 7 wherein the changing a treatment parameter includes changing a treatment parameter different than the leaf pattern of the multi-leaf collimator.

9. A method as set forth in claim 8 wherein the treatment parameter includes changing a timing of the multi-leaf collimator.

10. A method as set forth in claim 7 wherein the radiation therapy is delivered by a radiation therapy system including a gantry, and wherein the changing a treatment parameter includes changing a gantry parameter.

11. A method as set forth in claim 10 wherein the gantry parameter includes at least one of a gantry speed and a gantry direction.

12. A method as set forth in claim 7 wherein the radiation therapy is delivered by a radiation therapy system including a patient support, and wherein the changing a treatment parameter includes changing a patient-support parameter.

13. A method as set forth in claim 12 wherein the patient-support parameter includes at least one of a patient-support speed and a patient-support direction.

14. A method as set forth in claim 7 wherein the radiation therapy is delivered by a radiation therapy system including a radiation module having a jaw, and wherein the changing a treatment parameter further includes changing a jaw parameter.

15. A method as set forth in claim 14 wherein the jaw parameter includes at least one of a jaw position and a jaw direction.

16. A method as set forth in claim 8 wherein changing a treatment parameter includes changing the leaf pattern of the multi-leaf collimator from the leaf pattern as specified by the treatment plan while the radiation beam is active based at least in part on the monitoring the patient, and wherein the series of machine instructions includes a set of leaf open times and wherein the changing a leaf pattern includes scaling at least one of the machine instructions.

* * * * *